United States Patent
Englehart et al.

(10) Patent No.: US 11,030,081 B2
(45) Date of Patent: Jun. 8, 2021

(54) INTEROPERABILITY TEST ENVIRONMENT

(71) Applicant: Michigan Health Information Network Shared Services, East Lansing, MI (US)

(72) Inventors: Matthew Englehart, East Lansing, MI (US); Timothy Pletcher, Mount Pleasant, MI (US)

(73) Assignee: Michigan Health Information Network Shared Services, East Lansing, MI (US)

( * ) Notice: Subject to any disclaimer, the term of this patent is extended or adjusted under 35 U.S.C. 154(b) by 0 days.

(21) Appl. No.: 16/679,675

(22) Filed: Nov. 11, 2019

(65) Prior Publication Data

US 2020/0379885 A1    Dec. 3, 2020

Related U.S. Application Data

(60) Provisional application No. 62/854,072, filed on May 29, 2019.

(51) Int. Cl.
| | | |
|---|---|---|
| *G06F 11/36* | (2006.01) | |
| *G06F 21/53* | (2013.01) | |
| *G16H 40/40* | (2018.01) | |

(52) U.S. Cl.
CPC ...... *G06F 11/3664* (2013.01); *G06F 11/3684* (2013.01); *G06F 11/3688* (2013.01); *G06F 21/53* (2013.01); *G16H 40/40* (2018.01); *G06F 2221/033* (2013.01)

(58) Field of Classification Search
CPC ............ G06F 11/3664; G06F 11/3684; G06F 11/3688; G06F 21/53; G06F 2221/033
See application file for complete search history.

(56) References Cited

U.S. PATENT DOCUMENTS

| | | | | |
|---|---|---|---|---|
| 2007/0055543 A1* | 3/2007 | Knapp | ................... | G06Q 50/22 705/2 |
| 2011/0161063 A1* | 6/2011 | Pye | ..................... | G06F 11/3664 703/13 |
| 2015/0195724 A1* | 7/2015 | Leal | .................... | G06F 11/3664 370/242 |
| 2015/0370992 A1* | 12/2015 | Yao | ........................ | G06F 17/18 703/2 |

\* cited by examiner

*Primary Examiner* — Wei Y Zhen
*Assistant Examiner* — Amir Soltanzadeh
(74) *Attorney, Agent, or Firm* — Honigman LLP

(57) ABSTRACT

A method includes receiving, from a client device, configuration data for creating a collaboration environment for building and testing a software application. Based on the configuration data, the method includes generating a simulated network of simulated services and generating synthetic patient data configured to progress through the simulated network of simulated services. Each simulated service within the simulated network of services includes a set of resources. The method also includes transmitting visualization data associated with execution of the software application in the collaboration environment to the client device. The client device is configured to display the visualization data on a user interface.

20 Claims, 6 Drawing Sheets

INTEROPERABILITY TEST ENVIRONMENT

CROSS REFERENCE TO RELATED APPLICATIONS

This U.S. patent application claims priority under 35 U.S.C. § 119(e) to U.S. Provisional Application 62/854,072, filed on May 29, 2019. The disclosure of this prior application is considered part of the disclosure of this application and is hereby incorporated by reference in their entireties.

TECHNICAL FIELD

This disclosure relates to an interoperability test environment.

BACKGROUND

The demand for using synthetic patient data that is highly realistic, and clinically relevant, continues to increase for use in interoperability testing of healthcare-related services since there is no risk of disclosing protected health information (PHI), the transfer of which, is highly regulated, for example under the Health Insurance Portability and Accountability Act of 1996 (HiPAA), to protect the privacy of individuals. For instance, large scale synthetic patient data is useful for powering interoperability testing of services such as clinical quality measures and population health activities, while small scale bespoke "persona" data may be useful to power case driven interoperability testing of services such as medication reconciliation and gaps-in-care. Often, interoperability testing requires collaboration across multiple organizations and stake holders, such as, without limitations, physicians and physicians' groups, health care service providers, health insurance plans, hospital networks/companies, pharmacies, laboratories, government agencies, etc. As a result, before interoperability testing starts, there are often significant legal and governance hurdles that must be cleared between the collaborators prior to engaging in multi-organization interoperability testing. While Connectathon-like events provide exceptional venues for promoting interoperability between organizations, these events include a number of drawbacks. For instance, Connectathons typically have a set duration (e.g., two days) and may be cost prohibitive due to costs associated with marketing, fees to host venue, travel costs to host venue, test environment configuration, etc. Moreover, participants at Connectathons are typically required to be physically present at a same facility, while attendance is limited to those individuals that are able to travel to the host venue and capacity of the host venue.

SUMMARY

One aspect of the disclosure provides a method that includes receiving, at data processing hardware of a collaboration platform, from a client device, configuration data for creating a collaboration environment for building and testing a software application. Based on the configuration data: the method includes generating, by the data processing hardware a simulated network of simulated services; and generating, by the data processing hardware, synthetic patient data configured to progress through the simulated network of simulated services. Each simulated service within the simulated network of services includes a set of resources. The method also includes transmitting, by the data processing hardware, visualization data associated with execution of the software application in the collaboration environment to the client device. The client device is configured to display the visualization data on a user interface.

Implementations of the disclosure may provide one or more of the following optional features. In some implementations, the method also includes receiving, at the data processing hardware, one or more invitations from the client device inviting corresponding organizations access to the collaboration environment for building and testing the software application; and for each invitation of the one or more invitations, transmitting, by the data processing hardware, the invitation to the corresponding organization. The invitation includes authorization/authentication credentials for use by the corresponding organization to access the collaboration environment. The at least one of the simulated services executes on a Fast Healthcare Interoperability Resources (FHIR)-based server.

In some examples, the method also includes exposing, by the data processing hardware, a proprietary services to the collaboration environment through a corresponding sandbox. The proprietary service is configured to execute securely within the corresponding sandbox without exposing its contents to the collaboration platform.

In some implementations, generating the synthetic patient data includes generating a population of synthetic patients. The population of synthetic patients may be generated during a probability run. In additional implementations, the method also includes progressing, by the data processing hardware, one or more of the synthetic patients of the population through the simulated network of simulated services.

In some examples, generating the synthetic patient data includes obtaining one or more synthetic personas from a synthetic patient library, each synthetic persona comprising a synthetic representation of an individual. In these examples, the method may further include, for at least one synthetic persona of the one or more synthetic personas obtained from the synthetic patient library, receiving, at the data processing hardware, modification inputs from the client device to modify the synthetic representation of the individual of the at least one synthetic persona. In other examples, generating the synthetic patient data includes building one or more synthetic personas. Here, each synthetic persona includes synthetic representations of an individual specifically tailored for testing the software application.

Another aspect of the present disclosure provides a system that includes data processing hardware and memory hardware in communication with the data processing hardware and storing instructions, that when executed on the data processing hardware, cause the data processing hardware to perform operations that include receiving from a client device, configuration data for creating a collaboration environment for building and testing a software application. Based on the configuration data: the operations include generating a simulated network of simulated services; and generating synthetic patient data configured to progress through the simulated network of simulated services. Each simulated service within the simulated network of services includes a set of resources. The operations also include transmitting visualization data associated with execution of the software application in the collaboration environment to the client device. The client device is configured to display the visualization data on a user interface.

This aspect of the disclosure may provide one or more of the following optional features. In some implementations, the operations also include receiving one or more invitations from the client device inviting corresponding organizations access to the collaboration environment for building and testing the software application; and for each invitation of the one or more invitations, transmitting the invitation to the corresponding organization. The invitation includes authorization/authentication credentials for use by the corresponding organization to access the collaboration environment. The at least one of the simulated services executes on a Fast Healthcare Interoperability Resources (FHIR)-based server.

In some examples, the operations also include exposing a proprietary services to the collaboration environment through a corresponding sandbox. The proprietary service is configured to execute securely within the corresponding sandbox without exposing its contents to the collaboration platform.

In some implementations, generating the synthetic patient data includes generating a population of synthetic patients. The population of synthetic patients may be generated during a probability run. In additional implementations, the operations also include progressing one or more of the synthetic patients of the population through the simulated network of simulated services.

In some examples, generating the synthetic patient data includes obtaining one or more synthetic personas from a synthetic patient library, each synthetic persona comprising a synthetic representation of an individual. In these examples, the operations also include, for at least one synthetic persona of the one or more synthetic personas obtained from the synthetic patient library, receiving modification inputs from the client device to modify the synthetic representation of the individual of the at least one synthetic persona. In other examples, generating the synthetic patient data includes building one or more synthetic personas. Here, each synthetic persona includes synthetic representations of an individual specifically tailored for testing the software application.

The details of one or more implementations of the disclosure are set forth in the accompanying drawings and the description below. Other aspects, features, and advantages will be apparent from the description and drawings, and from the claims.

DESCRIPTION OF DRAWINGS

Like reference symbols in the various drawings indicate like elements.

DETAILED DESCRIPTION

Implementations herein are directed toward an interoperability testing environment that requires collaboration across different organizations and stakeholders and uses synthetic healthcare data for use in healthcare-related tests such as clinical quality measures and population health activities, as well as specific use case-driven testing related to medication reconciliation, gaps-in-care, etc. Accordingly, the interoperability testing environment provides a collaboration platform where multiple organizations can learn, build, and test healthcare applications and services with no risk of disclosing protected health information (PHI) since all testing leverages a simulated/virtual healthcare network populated with highly realistic, clinically relevant, synthetic/virtual patient data.

Figure 1:
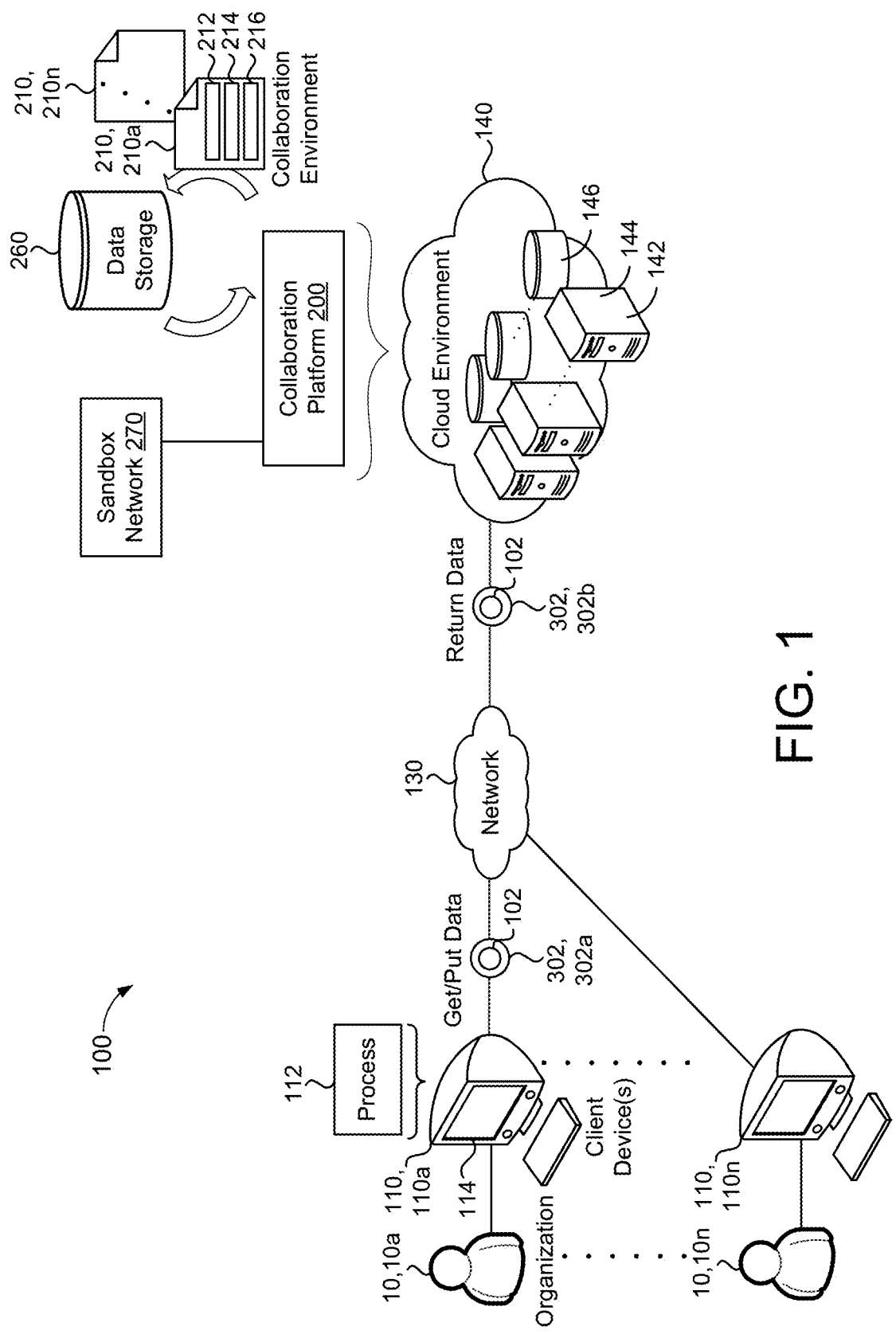
FIG. 1 is a schematic view of an interoperability testing environment including a collaboration platform interfacing with a plurality of client devices.

Referring to FIG. 1, in some implementations, a healthcare interoperability testing environment 100 includes multiple client devices 110, 110a-n associated with different entities/organizations 10, 10a-n, who may communicate, via network 130, with a collaboration platform 200 executing on a remote system 140. For instance, the client devices 110 may execute a client process 112 (e.g., a web-browser) that provides an interface 114 to communicate with the collaboration platform 200 on the remote system 140. The remote system 140 may be a distributed system (e.g., cloud computing environment) having scalable/elastic resources 142. The resources 142 include computing resources 144 (e.g., data processing hardware) and/or storage resources 146 (e.g. memory hardware). The remote system 140 may be associated with one or more cloud-service providers to host the collaboration platform 200 as a scalable, high availability, and economical test (and/or event) platform-as-a-service under a shared legal and governance framework. As a result, the collaboration platform 200 is able to drastically reduce costs associated with managing multiple test environments typically required for interoperability testing at in-person events, such as Connectathons, while also drastically minimizing legal, governance, and development efforts. As will become apparent, the collaboration platform 200 is able to leverage data visualization to create insight into interoperability issues across a broader set of organizations/stakeholders that include, without limitation, clinicians, developers, business leaders, patients, and others. Further, an organization 10 such as a third-party application developer, may utilize the collaboration platform 200 to promote community collaboration with events and structured challenges.

The collaboration platform 200 provides an interface for executing one or more collaboration environments 210, 210a-n within a secure execution environment. The interface provided by the collaboration platform 200 may include a Fast Healthcare Interoperability Resources (FHIR®) interface (or Application Program Interface (API)) associated with the FHIR interoperability standard for the transfer of data between software applications and various healthcare entities, databases, etc. FHIR is part of the Health Level 7 (HL7) standards propagated by the standards organization Health Level Seven International, Inc. Accordingly, and as discussed in greater detail with reference to FIGS. 2 and 3, the FHIR interface of the collaboration platform 200 may allow client devices 110 to configure a simulated healthcare network 300 that includes one or more simulated healthcare services 310 (e.g., FHIR servers) (FIG. 3) that communicate using the FHIR interoperability standard.

In some examples, the collaboration platform 200 wraps each collaboration environment 210 to serve as a proxy for communicating program calls 302 between the collaboration environment 210 and the client processes 112. Each collaboration environment 210 executing on the collaboration platform 200 may facilitate development, integration, acceptance, and testing of a service or software application 212 using innovative technologies as well as open standards. In one example, a collaboration environment 210 executing on the collaboration platform 200 enables multiple authorized/ authenticated organizations 10 to collaborate with one another to build and test a software application 212 for treating individuals with opioid addiction. Here, the organizations 10 may include any combination of a software developer, a payer (e.g., health insurance company), a health system (e.g., hospital company), and a health information exchange (HIE) that may access the collaboration platform 200 and use the collaboration environment 210 for building and testing the opioid addiction software application 212. The collaboration platform 200 may charge fees to each organization accessing a given collaboration platform 210. In some examples, a creator of a collaboration platform 210 is charged while other collaborators invited by the creator are not charged to access the collaboration environment 210. The collaboration platform 200 may include a tiered fee structure that collaborators may choose based on their usage needs. In some implementations, a collaboration of organizations 10 configures a simulated healthcare network 300 and synthetic patient data 226, 400 (FIG. 2) within a respective collaboration environment to develop and test a software application 212 under real world healthcare scenarios without ever accessing or disclosing protected health (PHI) information. The collaboration platform 200 may similarly allow organizations to create, configure, and manage event environments (e.g., Connectathons) with minimal dependency on technical resources through a simple user interface 114. The collaboration platform 200 may connect to commonly used healthcare platform APIs such as Blue Button 2.0, Epic, Cerner, or any other testing environment.

As used herein, the organizations 10 using the collaboration platform 200 to collaborate with one another may include, without limitation, providers, provider organizations, commercial health plans, government payers, universities, healthcare application development (app dev) companies), medical device manufacturers, technology incubators, health information technology (IT) vendors, standards development organizations (e.g., HL7), research institutes, health information exchanges (HIEs), labs, and pharmacies. Additionally, organizations may further include grant funded projects, industry associations, alliances, and consortiums, as well as government agencies (federal, state, and/or local). While many of the examples herein disclose the benefits of the collaboration platform 200 with respect to the healthcare industry, the benefits of the collaboration platform 200 can be applied broadly to other industries/ communities such as, without limitation, transportation, retail, manufacturing, energy, and others.

Each collaboration environment 210 may be associated with one or more respective software applications 212, a set of collaborators 214, and a state 216 of the collaboration environment 210. Here, the set of collaborators 214 may specify one or more organizations 10 collaborating with one another in the development and testing of the software application 212, as well as credentials/permissions of each organization 10 within the collaboration environment. For instance, one of the collaborators 214 may be an administrator that invites (e.g., through a structured "challenge") the other collaborators to the collaboration environment 210, whereby the other collaborators 214 may already be clients/ users of the collaboration platform 200. Additionally, an organization 10 may include multiple employees/users capable of accessing the collaboration environment 210, whereby some users may have different credentials/permissions for interacting in the collaboration environment 210.

For instance, some collaborators 214 may have read-only access, while others have only limited write capabilities. Accordingly, an administrator may create and manage collaborators access rights, permissions, and profiles. The state 216 of the collaboration environment 210 can be saved at any time, such that each collaboration environment 210 may be associated with multiple states 216 through the development, testing, and modification of the software application 212 over time. Some states 216 may be associated with different sets of collaborators 214 and/or configurations/ states of the simulated healthcare network 300. Each collaboration environment 210 may be stored in data storage 260 (e.g., memory hardware 146).

In some implementations, the collaboration platform 200 also provides an interface to a network of trusted sandboxes 270. Each sandbox 270 may provide an execution environment that is isolated from the collaboration platform 200, and may be associated with proprietary data or software services that an owner (e.g., one of the collaborators 214) may provide a specified collaboration environment 210 access for building and testing a software application 212. For instance, in the example above, the payer may wish to see how a proprietary claim-submission processing service executing in a trusted sandbox 270 integrates with the software application 212 in the collaboration environment 210. The network of trusted sandboxes 270 allows parties/ organizations 10 to keep their data and services isolated from the collaboration platform 200 and provide access to execution of services within those sandboxes 270 only under express permissions granted by the owner organization 10 that may be revoked at any time. Each sandbox 270 may be firewalled from outside intrusion to perform guarantees that data operated upon, or stored within, the sandbox is kept secret and confidential. Thus, one or more trusted sandboxes 270 may contain computation logic of a given collaboration environment 200 and corresponding software application 214 being tested. Advantageously, the functionality of the trusted sandbox 270 when integrated with the collaboration platform 200 alleviates legal/governance friction that often results when proprietary data is shared in multi-organizational frameworks.

Each client device 110 can be any computing devices capable of communicating with the remote system 140 through the network 130. The client device 110 includes, but is not limited to, desktop computing devices and mobile computing devices, such as laptops, tablets, smart phones, and wearable computing devices (e.g., headsets and/or watches). The client device 110 may correspond to a client/ organization 10 of the remote system 140 that uses the collaboration platform 200 to collaborate with other organizations 10 in a respective collaboration environment 210 to facilitate, build, and/or test a software application 212.

In the example shown, the client device 110 executes the client process 112 (e.g., via an application programming interface (API) 114) to initiate a program call 302, 302a to the collaboration platform 200. In some examples, the program call 302 may include configuration inputs for creating a collaboration environment 210 and invitations for soliciting/inviting other organizations to the collaboration environment 210. The client devices 112 associated with different organizations 10 and collaborating with one another within a respective collaboration environment 210 may provide program calls 302 to communicate with the collaboration platform 200. The program calls 302 may include put data calls that provide data 102 from the client devices 110 for input to the collaboration platform 200, as well as get data calls that return data 102 from the collaboration platform 200 to the client devices 110. In some examples, return data 102 includes visualization data related to interoperability testing, events, or other data shared between collaborators within a collaboration environment. The collaboration platform 200 may provide program calls 302, 302b to client devices 110 that provides a challenge request for authorizing and authenticating organizations 10 attempting to gain access to the collaboration platform 200, or more specifically, to a respective collaboration environment 210 executing in the collaboration platform 200. In some examples, a program call 302 is a representational state transfer (REST) call. Additionally or alternatively, some program calls may include a remote procedure call (RPC).

Figure 2:
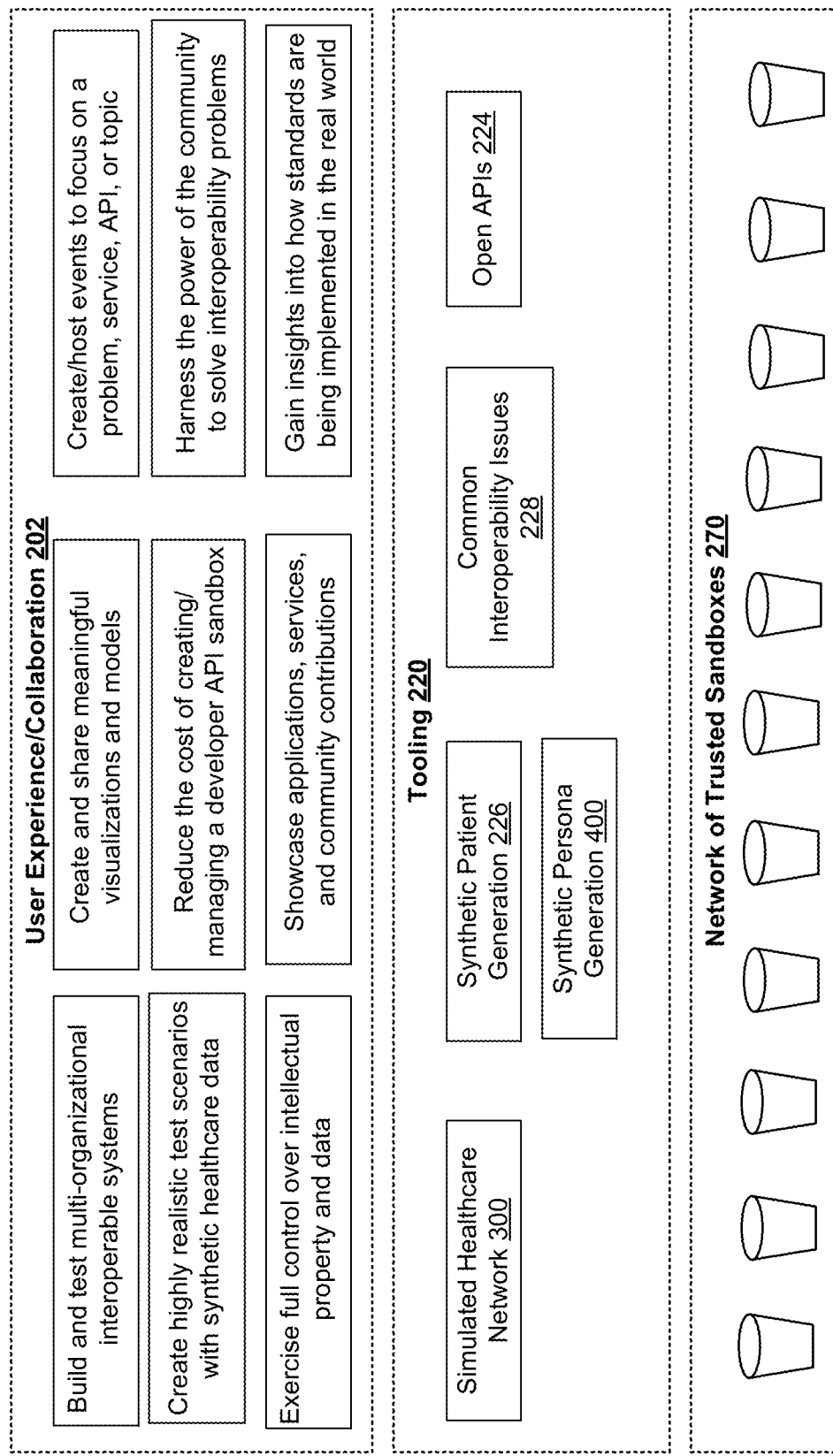
FIG. 2 is a schematic view of the collaboration platform of FIG. 1.

Referring to FIG. 2, an example architecture of the collaboration platform 200 is shown. The collaboration platform 200 may be organized into a user experience/collaboration level 202, a tooling level 220, and the network of trusted sandboxes 270. The user experience/collaboration level 202 provides a non-exhaustive list of core functionality of the collaboration platform 200. For instance, the platform 200 serves as a proxy for building and testing multi-organization interoperable systems (e.g., applications 212), creating/sharing meaningful visualizations and models between collaborators, and creating/hosting events to focus on a particular problem, service, API, or topic in a given industry (e.g., healthcare service industry). The platform 200 is configured to create highly realistic test scenarios using synthetic healthcare data (e.g., synthetic patient data 226, 400 and/or synthetic healthcare network data), while allowing collaborators to exercise full control over intellectual property, data, and other legal/governance issues. Advantageously, the secure execution environment offered by the collaboration platform 200 reduces costs that occur from requiring developers to create/manage a developer API sandbox for building and testing software applications. At the same time, the platform 200 showcases applications, services, and community contributions between a multi-organizational collaboration by harnessing a power of a community to solve interoperability problems that conventionally require physical meetings (e.g., "Connectathons") of the organizations to address the problems. As a result, the collaboration platform 200 affords organizations to gain valuable insights into how standards are being implemented in the real world without ever exposing or using personal health information. In fact, the collaboration platform 200 can be employed to enhance and optimize such Connectathon events to power interoperability demos and enable different organizations 10 to continue discussions for development, building, and testing of interoperable software applications 212 after conclusion of these Connectathon events. Similarly, new organizations can be invited at any time to join a collaboration environment 210 currently executing in the collaboration platform 200.

The tooling level 220 provides resources for creating, configuring, and managing collaboration environments 210 (e.g., interoperability test environments and/or interoperability event environments) with minimal effort and optimizing costs. In the example shown, the tooling level 220 includes a non-exhaustive list of resources/modules for creating, configuring, and managing a collaboration environment 220. In some implementations, an organization 10 or a collaboration of organizations selects, configures, and manages a simulated healthcare network 300 that includes one or more simulated healthcare services 310 (e.g., FHIR servers) (FIG. 3) that communicate using the FHIR interoperability standard. The simulated healthcare services 310 may emulate "edge" organizations like hospital companies, HIEs or healthcare plans. In some examples, the services 310 of the simulated healthcare network 300 and the APIs of the collaboration platform 200 interconnect using the OAuth 2.0 authorization framework. Additionally or alternatively, the collaboration platform 200 may interconnect to services 310 of the simulated healthcare network 300, trusted sandboxes, and/or open APIs 224 in remote systems using any real world authorization protocol such as SMART on FHIR, OAuth, or Open ID Connect.

Figure 3:
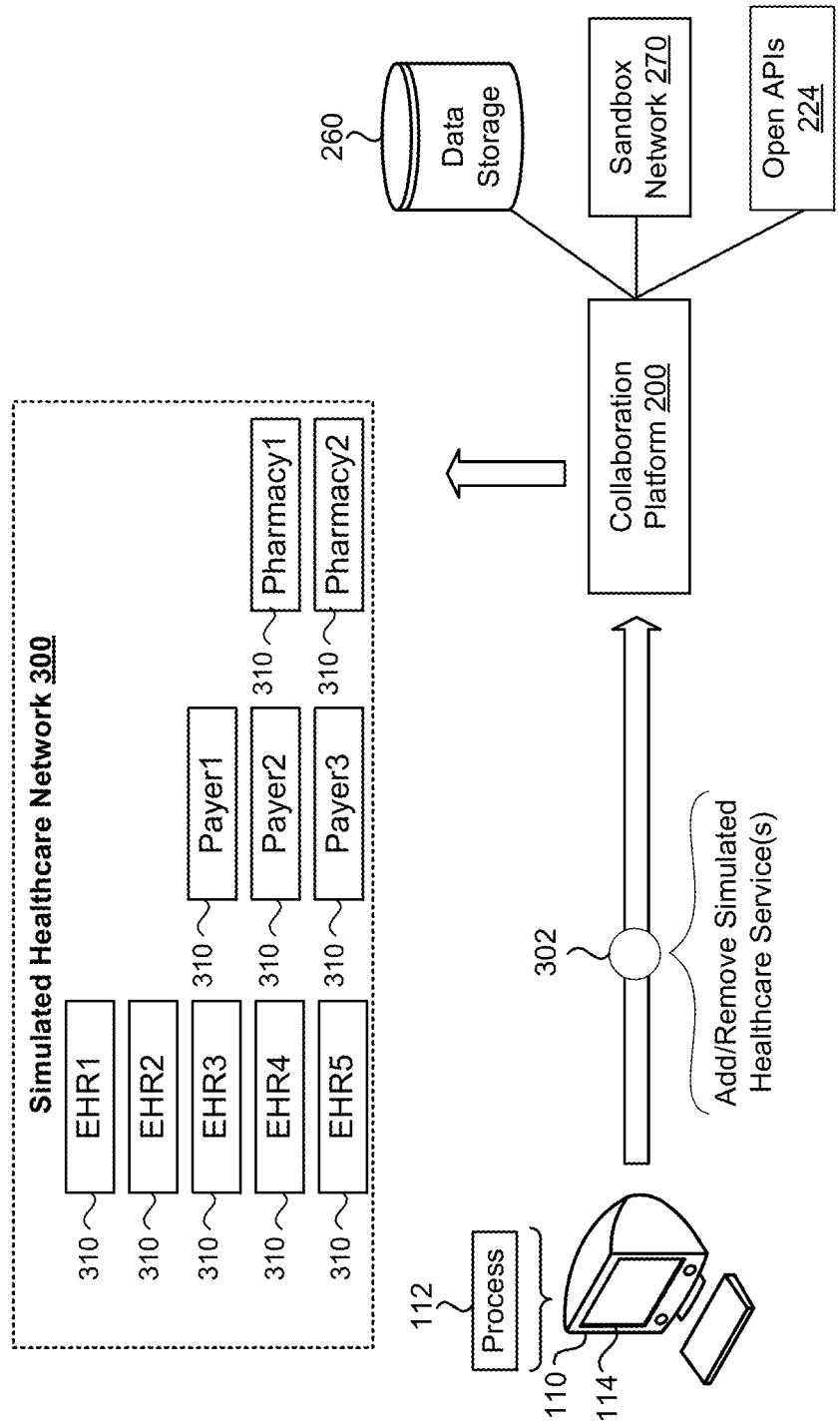
FIG. 3 is a schematic view of a simulated healthcare network that includes one or more simulated healthcare services.

FIG. 3 shows an example simulated healthcare network 300 configured by the tooling level 220 of the collaboration platform 200 to include a set of simulated healthcare services 310. The software application 212 under development or testing in a given collaboration environment 210 may connect to a simulated healthcare service 310 to simulate the application's 212 functionality with a respective service associated therewith. In the example shown, a client device 110 associated with one of the collaborators of the collaboration environment 210 may issue program calls 302 to the collaborating platform 200 that include configuration instructions for configuring the simulated healthcare network 300. Here, each simulated healthcare service 310 may be added or removed through corresponding program calls 302 issued by the client device 110. In some examples, the services 310 of the simulated healthcare network 300 are selected from a preconfigured list of synthetic healthcare services 310 each emulating a real-world healthcare service involved in treating a particular condition (e.g., opiate treatment, diabetes, etc.) In these examples, the preconfigured simulated healthcare services 310 are stored in the data storage 260 (e.g., memory hardware 146) and retrieved by the collaboration platform 200.

Moreover, proprietary services may be added to the simulated healthcare network 300 from the network of trusted sandboxes 270. For instance, one of the collaborators 214 may grant access to a proprietary service through the network of trusted sandboxes 270 to test functionality of the software application 212 with the proprietary service in the collaboration environment 214. In this scenario, the proprietary service is a "real service" executing in a "simulated" testing environment through a respective sandbox as one of the simulated healthcare services 310 of the simulated healthcare network 300. Additionally or alternatively, public or open source services may be added to the simulated healthcare network 300 through an open API 224. For instance, organizations may grant access to their services for use in collaboration environments 214 through open APIs 224 that may implement the FHIR interoperability standard. In some examples, these public or open source services start as beta proprietary services first accessed through a sandbox of the network of trusted sandboxes 270, and later released to the community of the collaboration platform 200 for use in simulated healthcare networks 300 configured for collaboration environments 210.

The client device 110 may configure and view the simulated healthcare network 300 through the API interface 214 executing on the client device 110. Each healthcare service 310 in the simulated network 300 may include a set of one or more resources. In some implementations, resources of each simulated healthcare service 310 are accessible responsive to an input indication indicating selection of the corresponding simulated healthcare service 210 via the API interface 214. For instance, the API interface 214 may include a graphical user interface (GUI) that allows a user to provide input (e.g., mouse, touch, button, speech, gaze, gesture, etc.) for selecting a respective service 210 to view contents thereof. In some examples, users (e.g., collaborator/ organization 10) are capable of modifying at least one resource in the set of resources for a respective healthcare service 310.

In the example shown, the simulated healthcare network 300 is associated with the treatment of a particular medical condition (e.g., treating opioid addiction) and includes five electronic health record (EHR) services 310 (EHR1, EHR2, EHR3, EHR4, EHR5), three payer services 310 (Payer1, Payer2, Payer3), and two pharmacy services 310 (Pharmacy1, Pharmacy2). The services 310 in the simulated healthcare network 300 may come pre-populated based on the software application 212 being built and tested. Each of these simulated healthcare services 310 may be synthetic services provided by the collaboration platform 200 that use the FIHR standard. Here, the EHR1 and EHR2 may be associated with two different hospital companies/networks that a hypothetical patient with the medical condition may access during treatment. The EHR3 may include an independent primary network that the hypothetical patient may visit in addition to, or in lieu of, either of the hospital companies/networks. The EHR4 may include a specialist network administration service, such as a drug therapist that specializes in treating the particular medical condition. In some examples, the EHR4 is preconfigured with basic therapist attributes and the collaborators may modify the attributes so that the EHR4 corresponds to a specialized drug therapist specifically tailored for treating opioid addiction. The EHR5 may correspond to a group therapy health service, such as a rehab center, detox center, or outpatient group therapy. As with the EHR4, the EHR5 may be configurable to align with the particular medical condition the underling collaboration environment 210 is being used to treat. Each Pharmacy1, Pharmacy2 may represent a different pharmacy that a hypothetical patient with opioid addiction may obtain medications (e.g., methadone) prescribed by any of the EHRs.

In one example, the EHR1 simulates a popular healthcare alliance on a FHIR-based server executing on the remote system 140 (or some other remote system in communication with the collaboration platform 200). Upon receiving a selection indication via the API interface, the EHR1 may populate the following set of resources associated with the EHR1: basic resources; procedure resources; encounter resources; observation resources; care plan resources; condition resources; diagnostic report resources; medication administration resources; medication request resources; patient resources; allergy intolerance resources, medication statement resources, practitioner resources, person resources, medication resources, device resources; and location resources. One or more of the resources can be modified or removed altogether from the collaboration environment. Additional resources can be added in some scenarios. Each simulated healthcare service may further indicate a server the service executes on, software version associated with the service, and/or a FHIR base link. The simulated service may further specify the FHIR specification and whether or not the service is open source, as well as a project that was used to build the simulated software service when the service is synthetic. Further, a history of execution of the simulated healthcare service 310 may be accessed at anytime to indicate a history of all resource types on the server. Here, a date range and resource limit may be specified to retrieve the history.

Each Payer1, Payer2, Payer3 may be associated with a different health insurance plan to simulate claim processing by each of a top-tier medical insurance plan, a medical plan simulating Medicaid, and a medical plan simulating universal healthcare. For instance, Payer1 may reimburse payments for medications purchased from Pharmacy1 but not Pharmacy 2. In additional examples, other simulated services such as government agencies, e.g., probation requirements specified by a court for individuals charged with opioid possession, may be configured as part of the simulated healthcare network 300.

Referring back to FIG. 2, the tooling level 220 of the collaboration platform 200 further includes a module for generating synthetic patients 226 for use in developing and testing healthcare software applications 212 in a collaboration environment 210. In some examples, the module for generating synthetic patients 226 includes a FHIR-compatible "safe" test data generator that produces realistic patient histories at scale. Thus, in these examples, the test data generator may include a corresponding software/service that the collaboration platform 200 can access for generating synthetic patients 226. Typically, synthetic patients 226 are generated at large scale to power testing of software applications 210 related to clinical quality measures, population health activities, etc. The module for generating synthetic patients 226 may support data exchange standards including, but not limited to, 31 FHIR resources (DSTU2, STU3, and R4) into FHIR servers or files, 12 CQL-based HEDIS Measure reports, HL7 V3 CCDS into files, and HL7 V2 ADTs, ORUs, VXUs into files. In some examples, the test data generator includes Michigan Health Information Network Shared Services (MiHIN) PatientGen™ test data generator. In some implementations, a population of synthetic patients 226 map to the simulated healthcare services 310 of the simulated healthcare network 300 to provide highly realistic test scenarios for the software application 212 under development in the collaboration environment 210. For instance, the synthetic patients 226 may progress through various health states via symptoms, encounters, observations, diagnoses, medications, and procedures over a configurable length of time. In some examples, the synthetic patients 226 provide clinically relevant case histories that use real U.S. population statistics based on patient demographics, incidence and prevalence of health conditions, complications, and mortality.

The tooling level 220 may be configured to integrate various standards, open API's, and various partner platforms. Partner platforms may be exposed through the open APIs 226.

In some implementations, the tooling level 220 executes a probabilistic run for configuring the synthetic patients 226 and the simulated healthcare network 300 by linking each synthetic patient 226 to each simulated healthcare service 310 and providing a probability of whether or not a case history indicates that a synthetic patient 226 is treated by, or interacts with, the simulated healthcare service 310 during the configurable length of time. The probability run may include multiple disease modules for determining a probability that a given synthetic patient 226 includes a given disease. Here, the synthetic patient 226 may be analyzed by each disease module in sequence. The disease modules may maintain duration, range, mutual exclusivity, and likelihoods for good clinical relevance. In some examples, the probability run treats all medical conditions/diseases independently in order to produce synthetic patients 226 with unusual histories. Based on the disease modules and/or configurations of the probabilistic run, each synthetic patient 226 generated may be assigned a probability of having cardiovascular diseases, Diabetes, infectious diseases (e.g., immunizations, STDs, Pneumonia, Infections, Pertussis, Zika), risk factors (e.g., smoking, alcohol use, BMI, lipids, hypertension, promiscuity, opioid abuse), aging and mortality (25 vital signs, allergies, injuries, depression, self-harm, dementia, gallstones, gout, arthritis, COPD), malignancy models, and pregnancy (contraceptives and conception, preeclampsia and eclampsia, fetal screening and complications, spontaneous abortion, postpartum complications, birth encounter and complications during birth). Each synthetic patient 226 may be further assigned probabilities for genetic traits such as gender, race, BRCA1, BRCA2, HTT, Hgbs, CFTR, HLA_B27, +56 less common mutations screened for in blood spot testing of newborns, as well as neonate outcomes such as Autism, Down Syndrome, Cystic Fibrosis, Huntington's Chorea, Sickle Cell Anemia, and Attention Deficit Disorder.

Figure 4:
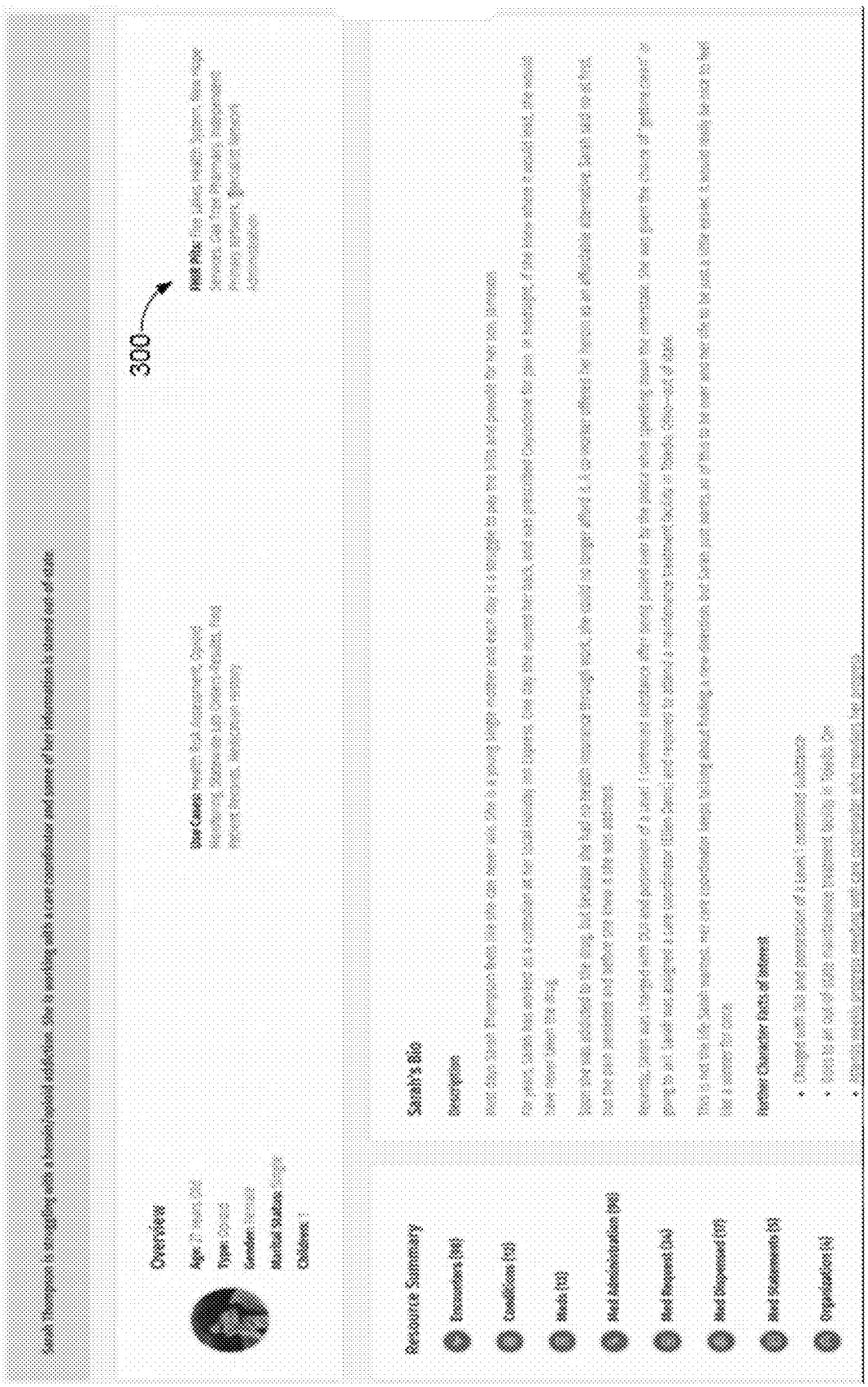
FIG. 4 is a schematic view of an example synthetic persona.

Referring to FIGS. 2 and 4, in some implementations, the tooling level 220 of the collaboration platform 200 further includes a module for generating synthetic personas 400 for use in developing and testing healthcare software applications 212 in a collaboration environment 210. In some examples, the tooling level 220 provides access to a library of synthetic personas 400 (e.g., stored on the memory hardware 146) to select from for use in testing a healthcare software application 212 in a respective collaboration environment 210. For instance, when the healthcare software application 212 under development and testing is associated with treatment of a particular disease or medical condition, synthetic personas 400 having the particular disease or medical condition may be retrieved. Typically, synthetic personas 400 are generated at small scale to power testing of use case-driven testing of software applications 210 related to medication reconciliation, gaps-in-care, etc. Attributes of the synthetic personas 400 may be edited so that the synthetic personas can be specifically tailored to interact with the collaboration platform 200. Additionally or alternatively, collaborators 214 in the collaboration environment 210 may build/generate custom synthetic personas 400 to apply to specific use cases that the corresponding healthcare software application 212 may encounter. An organization 10 collaborating in a collaboration environment 210 may browse, view, and configure synthetic personas 400 aligned to common use cases to facilitate prototyping, testing, event hosting, and demos.

FIG. 4 shows an example synthetic persona 400 that may be used for testing a healthcare software application 212. Here, the synthetic persona 400 may be displayed on the user interface 114 of a client device 110 collaborating in a collaboration environment 210 associated with the healthcare software application 212. A synthetic persona 400 provides a realistic and complete synthetic representation of a person/individual. For instance, and as opposed to synthetic patients 226 generated for large scale testing, a synthetic persona 400 provides unique attitudes, conditions, and environments that affect how the person/individual interact with the simulated healthcare network 300 configured for developing and testing the software application 212.

In the example shown, the synthetic persona 400 is for an individual named "Sarah Thompson" and includes a summary indicating that Sarah Thompson struggles with heroin/opioid addiction and is currently working with a care coordinator and some of her information is stored out-of-state. Here, the synthetic persona 400 aligns with the above example for development and testing of the software application 212 directed toward treating individuals with opioid addiction. The synthetic persona 400 provides an overview indicating an age (e.g., 27 years old), condition type (e.g., Opioid), gender (e.g., Female), marital status (e.g., single), and children (e.g., 1). The overview further provides one or more use cases associated with the synthetic persona 400 such as health risk assessment, opioid monitoring, statewide lab orders-results, find patient records, and medication history. In some examples, the overview additionally provides the simulated healthcare network 300 configured for developing and testing the software application. Any of these attributes can be modified to specifically tailor the synthetic persona to align with testing.

In contrast to synthetic patients 226, each synthetic persona 400 includes a corresponding biography for the synthetic individual that may update over time while the individual is under treatment (e.g., opioid treatment). The synthetic persona 400 may further provide a summary of resources associated with the individual. For instance, the summary of resources may indicate encounters, conditions, medications, med administration, med request, med dispensed, med statements, and organization. The summary of resources may update over time.

Referring back to FIG. 2, in some implementations, the tooling level 220 provides organization specific certifications to expose specific services to collaboration environments through an open API 224. These services may be freely accessed through the open API 224 and added to the simulated healthcare network 300 for testing a corresponding software application 212 between a collaboration of organizations 10. Further, the tooling level 220 further provides a library of common interoperability issues and challenges (e.g., FHIR interoperability issues and challenges) that are common in the real-world that collaborators may discover and test against in the collaboration environment 210. For instance, some FHIR-based servers may include data fields that do not recognize or accept text entered in all caps. In this scenario, the software application 212 may be configured to always input text in lowercase so that text entered in data fields of these FHIR-based servers is always recognized.

The collaboration platform 200 further includes the network of trusted sandboxes 270 level. In some examples, organizations collaborating in a given collaboration environment 210 for testing a software application 212 are capable of exposing propriety services to the collaboration environment 210 through a corresponding sandbox 270. Here, the proprietary service may execute securely within the corresponding sandbox without ever exposing its contents, while at the same time, the collaboration platform 200 is able to seamlessly integrate the proprietary service within the sandbox for testing in the collaboration environment 210. As a result, developers are not required to build custom API-sandbox for integrating proprietary services into the collaboration platform, nor are shared legal agreements required for using the proprietary services for testing since contents of the proprietary service are firewalled.

While a simulated healthcare network 300 is illustrated, a similar simulated network can be established for other industries, such as financial, that include a set of simulated services associated with that industry without departing from the scope of the present disclosure. For instance, in the financial industry, simulated networks could include banking institutions, credit agencies, credit card companies, loan servicers, government (local treasuries and IRS), etc. These simulated financial services could execute on servers that comply with some financial communication protocol. At the same time, synthetic borrowers and synthetic personas related to financial industry could be generated to align with a simulated financial network.

Moreover, the collaboration platform 200 may provide software as a service (SaaS) functionality in which collaboration environment 210 (or specific instance/state 216) created between two or more collaborators can be distributed to other platforms. For instance, one of the collaborators may use the collaboration platform 200 to develop, build, and test a software application 212 in a respective collaboration environment 210, and then distribute the collaboration environment 210 running the software application 212 to another platform associated with the collaborator. In this instance, the respective collaboration environment 210 may be licensed as SaaS from an owner of the collaboration platform 200. Additionally, a simulated service (e.g., simulated healthcare service 210) generated in a collaboration environment 210 can also be distributed by the collaboration platform 200 to other platforms for use thereon, and then returned back to collaboration environment 210 of the collaboration platform 200.

Figure 5:
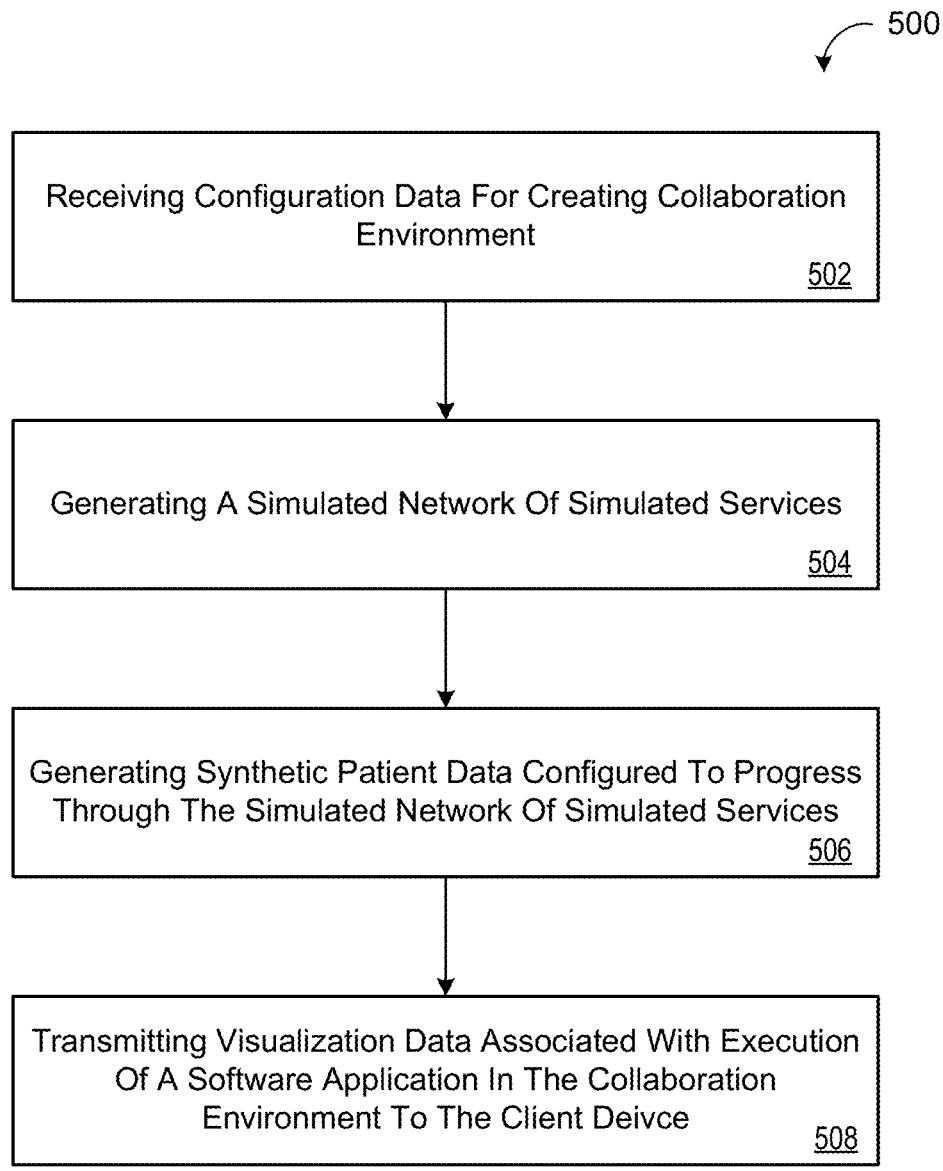
FIG. 5 is a flowchart of an example arrangement of operations for a method of creating a collaboration environment for building and testing a software application.

FIG. 5 provides a flowchart of an example arrangement of operations for a method 500 of creating a collaboration environment 210 for building and testing a software application 212. The method 500 may be executed on the data processing hardware 144 of the remote system 140 based on instructions stored on the memory hardware 146 of the remote system. At operation 502, the method 500 includes receiving, from a client device 110, configuration data 102, 302a for creating the collaboration environment 210 for building and testing the software application 212.

At operation 504, based on the configuration data 102, the method 500 includes generating a simulated network 300 of simulated services 310. Here, each simulated service 310 within the simulated network 300 of services includes a set of resources. At operation 506, based on the configuration data 102, the method 500 includes generating synthetic patient data 226, 400 configured to progress through the simulated network 300 of simulated services 310.

At operation 508, the method 500 includes transmitting visualization data 102, 302b associated with execution of the software application 212 in the collaboration environment 210 to the client device 110. The client device 210 is configured to display the visualization data 102 on a user interface 114. In some examples, the client device 110 executes a process 112 (e.g., a web-browser) that provides the user interface 114 to communicate with the data processing hardware 144 (e.g., executing the collaboration platform 200) on the remote system 140.

A software application (i.e., a software resource) may refer to computer software that causes a computing device to perform a task. In some examples, a software application may be referred to as an "application," an "app," or a "program." Example applications include, but are not limited to, system diagnostic applications, system management applications, system maintenance applications, word processing applications, spreadsheet applications, messaging applications, media streaming applications, social networking applications, and gaming applications.

The non-transitory memory may be physical devices used to store programs (e.g., sequences of instructions) or data (e.g., program state information) on a temporary or permanent basis for use by a computing device. The non-transitory memory may be volatile and/or non-volatile addressable semiconductor memory. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

Figure 6:
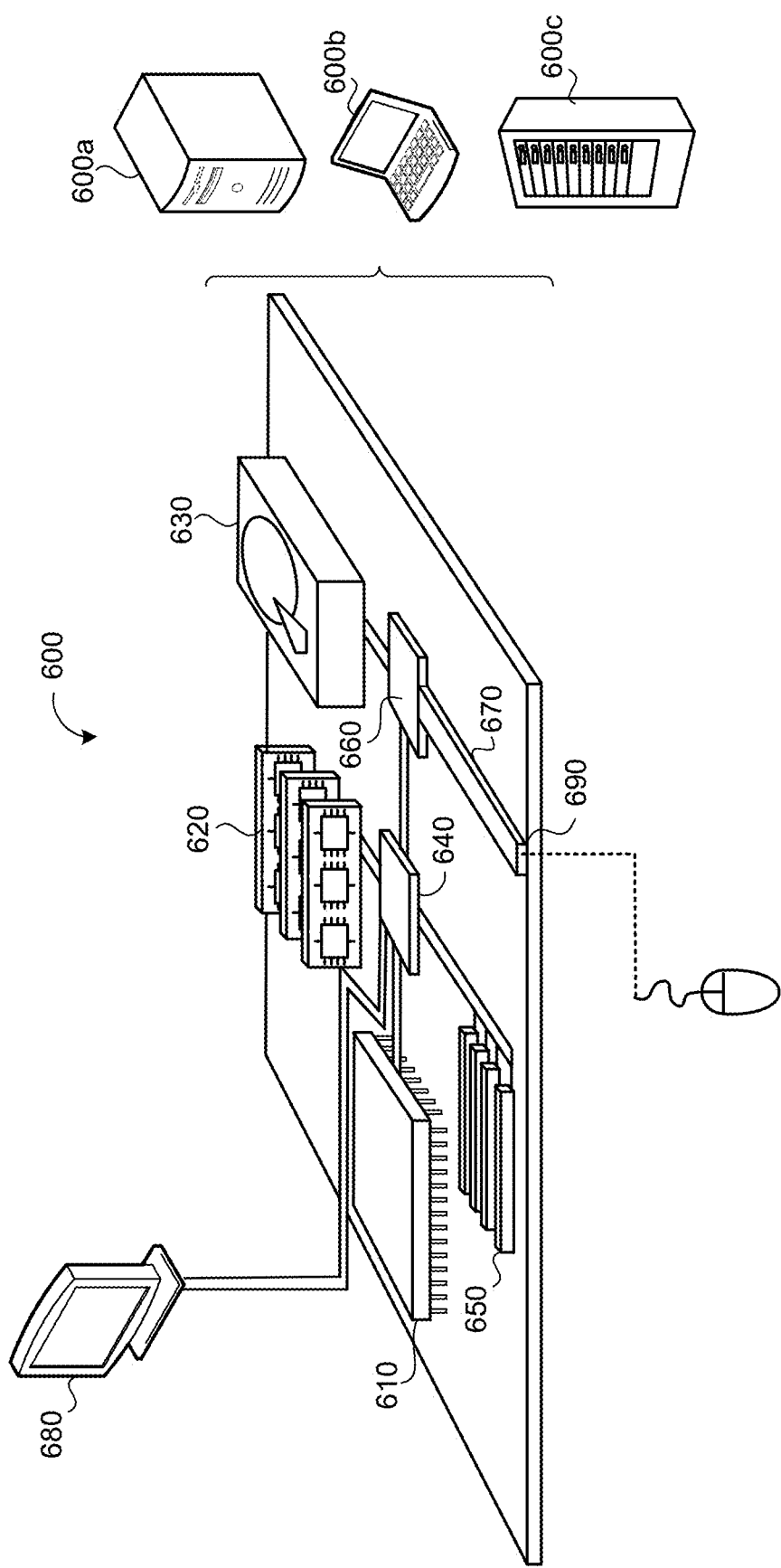
FIG. 6 is a schematic view of an example computing device that may be used to implement the systems and methods described herein.

FIG. 6 is schematic view of an example computing device 600 that may be used to implement the systems and methods described in this document. The computing device 600 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the inventions described and/or claimed in this document.

The computing device 600 includes a processor 610, memory 620, a storage device 630, a high-speed interface/controller 640 connecting to the memory 620 and high-speed expansion ports 650, and a low speed interface/controller 660 connecting to a low speed bus 670 and a storage device 630. Each of the components 610, 620, 630, 640, 650, and 660, are interconnected using various busses, and may be mounted on a common motherboard or in other manners as appropriate. The processor 610 can process instructions for execution within the computing device 600, including instructions stored in the memory 620 or on the storage device 630 to display graphical information for a graphical user interface (GUI) on an external input/output device, such as display 680 coupled to high speed interface 640. In other implementations, multiple processors and/or multiple buses may be used, as appropriate, along with multiple memories and types of memory. Also, multiple computing devices 600 may be connected, with each device providing portions of the necessary operations (e.g., as a server bank, a group of blade servers, or a multi-processor system).

The memory 620 stores information non-transitorily within the computing device 600. The memory 620 may be a computer-readable medium, a volatile memory unit(s), or non-volatile memory unit(s). The non-transitory memory 620 may be physical devices used to store programs (e.g., sequences of instructions) or data (e.g., program state information) on a temporary or permanent basis for use by the computing device 600. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The storage device 630 is capable of providing mass storage for the computing device 600. In some implementations, the storage device 630 is a computer-readable medium. In various different implementations, the storage device 630 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described above. The information carrier is a computer- or machine-readable medium, such as the memory 620, the storage device 630, or memory on processor 610.

The high speed controller 640 manages bandwidth-intensive operations for the computing device 600, while the low speed controller 660 manages lower bandwidth-intensive operations. Such allocation of duties is exemplary only. In some implementations, the high-speed controller 640 is coupled to the memory 620, the display 680 (e.g., through a graphics processor or accelerator), and to the high-speed expansion ports 650, which may accept various expansion cards (not shown). In some implementations, the low-speed controller 660 is coupled to the storage device 630 and a low-speed expansion port 690. The low-speed expansion port 690, which may include various communication ports (e.g., USB, Bluetooth, Ethernet, wireless Ethernet), may be coupled to one or more input/output devices, such as a keyboard, a pointing device, a scanner, or a networking device such as a switch or router, e.g., through a network adapter.

The computing device 600 may be implemented in a number of different forms, as shown in the figure. For example, it may be implemented as a standard server 600a or multiple times in a group of such servers 600a, as a laptop computer 600b, or as part of a rack server system 600c.

Various implementations of the systems and techniques described herein can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The processes and logic flows described in this specification can be performed by one or more programmable processors, also referred to as data processing hardware, executing one or more computer programs to perform functions by operating on input data and generating output. The processes and logic flows can also be performed by special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A number of implementations have been described. Nevertheless, it will be understood that various modifications may be made without departing from the spirit and scope of the disclosure. Accordingly, other implementations are within the scope of the following claims.

What is claimed is:
1. A method comprising:
receiving, at data processing hardware of a collaboration platform, from a client device, configuration data for creating a collaboration environment for building and testing a software application associated with treatment of a particular disease or medical condition;
based on the configuration data:
generating, by the data processing hardware, a simulated network of simulated services, each simulated service within the simulated network of services comprising a set of resources;
obtaining, by the data processing hardware, one or more synthetic personas configured to progress through the simulated network of simulated services, each synthetic persona comprising a respective synthetic representation of an individual; and
receiving, at the data processing hardware, from the client device, modification inputs to modify the synthetic representation of the individual of at least one of the one or more synthetic personas to specifically tailor the at least one of the one or more synthetic personas to align with building and testing the software application; and
transmitting, by the data processing hardware, visualization data associated with execution of the software application in the collaboration environment to the client device, the client device configured to display the visualization data on a user interface.

2. The method of claim 1, further comprising:
receiving, at the data processing hardware, one or more invitations from the client device inviting corresponding organizations access to the collaboration environment for building and testing the software application; and
for each invitation of the one or more invitations, transmitting, by the data processing hardware, the invitation to the corresponding organization.

3. The method of claim 2, wherein the invitation comprises authorization/authentication credentials for use by the corresponding organization to access the collaboration environment.

4. The method of claim 1, wherein at least one of the simulated services executes on a Fast Healthcare Interoperability Resources (FHIR)-based server.

5. The method of claim 1, further comprising, exposing, by the data processing hardware, a proprietary to the collaboration environment through a corresponding sandbox, the proprietary service configured to execute securely within the corresponding sandbox without exposing its contents to the collaboration platform.

6. The method of claim 1, further comprising, based on the configuration data, generating, by the data processing hardware, a population of synthetic patients during a probability run.

7. The method of claim 6, further comprising progressing, by the data processing hardware, one or more of the synthetic patients of the population through the simulated network of simulated services.

8. The method of claim 1, wherein obtaining the one or more synthetic personas comprises retrieving the one or more synthetic personas from a synthetic patient library.

9. The method of claim 8, wherein each synthetic persona retrieved from the synthetic patient library comprises the respective synthetic representation of an individual having the particular disease or medical condition associated with the software application.

10. The method of claim 1, wherein obtaining the one or more synthetic personas comprises building the one or more synthetic personas to apply specific use cases that the software application will encounter during execution of the software application in the collaboration environment.

11. A system comprising:
data processing hardware of a collaboration platform; and
memory hardware in communication with the data processing hardware, the memory hardware storing instructions that when executed on the data processing hardware cause the data processing hardware to perform operations comprising:
receiving, from a client device, configuration data for creating a collaboration environment for building and testing a software application associated with treatment of a particular disease or medical condition;
based on the configuration data:
generating a simulated network of simulated services, each simulated service within the simulated network of services comprising a set of resources;
obtaining one or more synthetic personas configured to progress through the simulated network of simulated services, each synthetic persona comprising a respective synthetic representation of an individual; and
receiving, from the client device, modification inputs to modify the synthetic representation of the individual of at least one of the one or more synthetic personas to specifically tailor the at least one of the one or more synthetic personas to align with building and testing the software application; and
transmitting visualization data associated with execution of the software application in the collaboration environment to the client device, the client device configured to display the visualization data on a user interface.

12. The system of claim 11, wherein the operations further comprise:
receiving one or more invitations from the client device inviting corresponding organizations access to the collaboration environment for building and testing the software application; and
for each invitation of the one or more invitations, transmitting the invitation to the corresponding organization.

13. The system of claim 12, wherein the invitation comprises authorization/authentication credentials for use by the corresponding organization to access the collaboration environment.

14. The system of claim 11, wherein at least one of the simulated services executes on a Fast Healthcare Interoperability Resources (FHIR)-based server.

15. The system of claim 11, wherein the operations further comprise exposing a proprietary service to the collaboration environment through a corresponding sandbox, the proprietary service configured to execute securely within the corresponding sandbox without exposing its contents to the collaboration platform.

16. The system of claim 11, wherein the operations further comprise, based on the configuration data, generating a population of synthetic patients during a probability run.

17. The system of claim 16, wherein the operations further comprise generating one or more of the synthetic patients of the population through the simulated network of simulated services.

18. The system of claim 11, wherein obtaining the one or more synthetic personas comprises retrieving the one or more synthetic personas from a synthetic patient library.

19. The system of claim 18, wherein each synthetic persona retrieved from the synthetic patient library comprises the respective synthetic representation of an individual having the particular disease or medical condition associated with the software application.

20. The system of claim 11, wherein obtaining the one or more synthetic personas comprises building the one or more synthetic personas to apply specific use cases that the software application will encounter during execution of the software application in the collaboration environment.

* * * * *